United States Patent [19]

Kondo et al.

[11] Patent Number: 4,849,557
[45] Date of Patent: Jul. 18, 1989

[54] PREPARATION OF TRIFLUOROMETHYLTOLUENE FROM HALOMETHYLBENZOTRIFLUORIDE

[75] Inventors: Takeshi Kondo, Sayama; Junji Negishi, Kawagoe; Yoshihiko Goto, Kamifukuoka; Matsue Minezaki; Toshikazu Kawai, both of Kawagoe, all of Japan

[73] Assignee: Central Glass Company, Limited, Ube, Japan

[21] Appl. No.: 193,061

[22] Filed: May 12, 1988

[30] Foreign Application Priority Data

May 13, 1987 [JP] Japan .................................. 62-114714
Jan. 29, 1988 [JP] Japan .................................. 63-17275

[51] Int. Cl.$^4$ ...................... C07C 17/24; C07C 17/38; C07C 21/24; C07C 17/00
[52] U.S. Cl. ..................................... 570/177; 570/144
[58] Field of Search .............................. 570/144, 177

[56] References Cited

U.S. PATENT DOCUMENTS 3,381,041  4/1968  Kometumi et al. ................. 570/177
4,558,166  12/1985  Baasner et al. ...................... 570/144

FOREIGN PATENT DOCUMENTS 705056  3/1965  Canada ................................ 570/144

*Primary Examiner*—J. E. Evans
*Attorney, Agent, or Firm*—Fleit, Jacobson, Cohn & Price

[57] ABSTRACT

Trifluoromethyltoluene is obtained from a halomethylbenzotrifluoride, which is a relatively inexpensive material, by hydrogenating the halomethyl group of the starting compound to methyl group with hydrogen gas in the presence of a hydrogenation catalyst and an acid acceptor. Suitable examples of the halomethyl group to be hydrogenated are —CH$_2$Cl, —CH$_2$F, —CHClF, —CClF$_2$ and —CF$_3$. When the starting compound is bis(trifluromethyl)benzene, addition of either an alcohol or an alkali metal fluoride to the reaction system is effective for suppression of formation of xylene as a by-product, and xylene still contained in the reaction product can completely be removed by treatment with a sulfonating agent such as fuming sulfuric acid.

17 Claims, No Drawings

PREPARATION OF TRIFLUOROMETHYLTOLUENE FROM HALOMETHYLBENZOTRIFLUORIDE

BACKGROUND OF THE INVENTION

This invention relates to a process of preparing trifluoromethyltoluene from a relatively inexpensive compound, viz. a halomethylbenzotrifluoride.

Trifluoromethyltoluene (abbreviated to TFMT) is useful as an intermediate material for preparing medicines and argicultural chemicals.

According to FR No. 1,522,956, 4-TFMT is obtained by reacting 4-trifluoromethylbenzyl alcohol in acetic acid with hydrogen gas in the presence of PdO. However, the starting compound of this process is a very expensive material.

It is also possible to obtain TFMT by reacting a methylphenyl compound with a selected flouride. For example, reaction of 4-methylbenzoic acid with $SF_4$ gives 4-TFMT. However, this reaction has to be carried out under high-temperatuare and high-pressure conditions, and $SF_4$ is expensive and very toxic and is not readily available as an industrial material. Another laboratory process is reacting iodotoluene with $CF_3I$ in the presence of $CuSO_4$, but this method is not suited to industrial practice because of high price of $CF_3I$. Reaction of toluene with carbon tetrachloride and hydrogen fluoride also gives TFMT. All the reactants in this process are relatively inexpensive, but the product of this process is always a mixture of 2-TFMT, 3-TFMT and 4-TFMT (e.g., 13:42:45) difficult to separate and purify.

SUMMARY OF THE INVENTION

It is an object of the present invention to provide a novel process for easily and efficiently preparing any of 2-TFMT, 3-TFMT and 4-TFMT from are relatively inexpensive starting material.

According to the invention, trifluoromethyltoluene is prepared by a process comprising reacting a halomethylbenzotrifluoride with hydrogen gas in the presence of an acid acceptor and a hydrogenation catalyst to thereby hydrogenate the halomethyl group of the starting compound to methyl group.

As the starting compound for this process it is preferred to select a halomethylbenzotrifluoride represented by the following general formula:

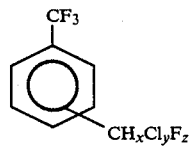

wherein x is 0, 1 or 2, y is 0, 1, 2 or 3 and z is 0, 1, 2 or 3, with proviso that the sum of x, y and z is 3.

A halomethylbenzotrifluoride (abbreviated to HMBTF) represented by the above general formula can easily be obtained from xylene, which is an inexpensive industrial material.

The hydrogenation reaction according to the invention an be carried out in an autoclave type reactor by first charging the reactor with HMBTF, an acid acceptor, a conventional hydrogenation catalyst and a liquid medium which may be either water or an inactive organic solvent, and, while heating and stirring these materials, passing hydrogen gas through the reactor until hydrogen is no longer absorbed in the reaction system under the employed temperature and pressure conditions. Generally, the reaction temperature is from 40° to 150° C. and the hydrogen gas pressure is from 1 to 50 kg/cm$^2$. The starting material for this process may be any of 2-HMBTF, 3-HMBTF and 4-HMBTF according to the kind of aimed TFMT. In any case a desired isomer of TFMT of high purity is obtained at very high yield.

However, when the starting HMBTF is bis(trifluoromethyl)benzene the yield of TFMT is relatively low because a considerable portion of the starting compound is hydrogenated at the both trifluoromethyl groups to turn into xylene, and it is difficult to isolate TFMT of high purity from the crude product since the boiling point of the aimed TFMT is close to that of the by-produced xylene. The present invention includes a solution of this problem. This is, the formation of xylene can be suppressed by carrying out the above described hydrogenation reaction in the presence of either an alcohol or an alkali metal fluoride. Although there is a limit to the effect of this measure so that a small amount of by-produced xylene still exists in the reaction product, that xylene can easily and completely be remvoed by sulfonating it. Therefore, it is fully practicable to use bis(trifluoromethyl)benzene as the most economical starting material for the process according to the invention. It is optional to do removal of by-produced xylene by sulfonation after carrying out the hydrogenation reaction without taking any measure for suppression of formation of xylene, but the object is accomplished more easily and efficiently by using an alcohol or an alkali metal fluoride in the reaction to minimize formation of xylene.

DESCRIPTION OF THE PREFERRED EMBODIMENTS

In the hydrogenation reaction according to the invention an acid acceptor is used to keep the reaction medium neutral or basic. The acid acceptor can be selected from various and ordinary bases such as hydroxides, carbonates, and acetates of alkali metals, hydroxides, oxides, carbonates and acetates of alkaline earth metals, ammonia and amines. Usually it is convenient to use an alkali metal salt such as sodium hydroxide, sodium carbonate, potassium hydroxide, potassium carbonate or lithium carbonate or an alkaline earth metal oxide such as calcium oxide or magnesium oxide. In generally the quantity of the acid acceptor should be at least equivalent by mol to the total halogens of the halomethyl group of the HMBTF to be hydrogenated.

The hydrogenation reaction is usually carried out in a liquid medium which is inactive to the reactants and the reaction product. The liquid medium may be either water or an organic liquid which can be selected from alcohols, ethers, hydrocarbons and acetic acid. In the case of an organic liquid medium it is preferable to make selection from $C_1$ to $C_6$ alcohols such as methanol, ethanol, isopropanol and 2-butanol. It is possible to use a mixture of two or more kinds of liquids. The concentration of the starting HMBTF in the liquid medium is very widely variable.

The hydrogenation catalyst for use in this invention is selected from commonly used ones such as palladium, platinum and nickel, and it is preferred to use a palladium catalyst carried on active carbon. It is suitable that the hydrogenation catalyst, as metal, amounts to 0.01–30 wt % and preferably 1–20 wt % of HMBTF sujected to hydrogenation.

For accomplishment of the desired hydrogenation a practicable range of the reaction temperature is from 40° to 150° C., and a preferable range is from 70° to 120° C. In the reactor the hydrogen gas pressure is maintained in the range from 1 to 50 kg/cm$^2$, and preferably in the range from 3 to 20 kg/cm$^2$.

When bis(trifluoromethyl)benzene is used as the starting HMBTF it is preferred to add either an alcohol or an alkali metal fluoride to the reaction system for the reason explained hereinbefore. If desired, an alcohol and an alkali metal fluoride may be used jointly. It suffices to use a relatively small quantity of alcohol or alkali metal fluoride may be used jointly. It suffices to use a relatively small quantity of alcohol or alkali metal fluroide. Alcohols very suitable for this purpose are C$_1$ to C$_6$ alcohols represented by methanol and ethanol. A suitable quantity of the alcohol is 0.1–10 wt %, and preferably 3–5 wt %, of the bis(trifluoromethyl)benzene. As to the alkali metal fluoride, use of potassium fluoride or sodium fluoride is preferred. A suitable quantity of the alkali metal fluoride is 3–10 wt % of the bis-(trifluoromethyl)benzene.

After hydrogenating bis(trifluoromethyl)benzene preferably in the presence of an alcohol and/or an alkali metal fluoride, the reaction product can be purified by sulfonating and thereby removing xylene formed in a small quantity as a by-producte. The sulfonation can be accomplished by using an ordinary sulfonating agent such as fuming sulfuric acid, concentrated sulfuric acid or chlorosulfonic acid. Of course the required minimum quantity of the sulfonating agent is equimolar to the xylene contained in the reaction product. It is desirable to perform the sulfonating treatment at a relatively low temperature to thereby avoid loss of the aimed product, TFMT.

the invention is further illsutrated by the following nonlimitative examples.

EXAMPLE 1

A 500-ml autoclave provided with a stirrer was charged with 100 g (0.514 mol) of 2-trifluoromethylbenzyl chloride, 164 g of 15 wt % aqueous solution of sodium hydroxide and 5 g of palladium-on-carbon catalyst (Pd: 5 wt %), and the atmosphere in the autoclave was replaced by hydrogen gas. Then the temperature in the autoclave was kept at 75° C. and the gas pressure at 8 kg/cm$^2$, and stirring was continued for 3 hr to thereby accomplish hydrogenation reaction. After the reaction the palladium catalyst was filtered out with a filter paper, and the filtrate was allowed to separate into an organic layer and an aqueous layer. The organic layer was dried wtih anhydrous sodium chloride to thereby obtain 77.0 g of 2-TFMT of 99.7% purity. The yield was 93.3%.

EXAMPLE 2

100 g of 3-trifluoromethylbenzyl choloride was used as the starting material. Otherwise, the process of Example 1 was repeated. As the result 76.1 g of 3-TFMT of 99.2% purity was obtained. The yield was 91.8%.

EXAMPLE 3

In this case 100 g (0.562 mol) of 4-trifluoro-methylbenzyl fluoride was used as the starting compound, and the process of Example 1 was repeated except that the quantity of the 15 wt % solution of sodium hydroxide was increased to 180 g. As the result 83.7 g of 4-TFMT of 99.3% purity was obtained. THe yeidl was 92.5%.

EXAMPLE 4

In this case 100 g (0.437 mol) of 2-trifluoro-methylbenzal chloride as used as the starting compound, and the process of Example 1 was repeated except that the quantity of the 15 wt % solution of sodium hydroxide was increased to 280 g. As the result 64.5 g of 2-TFMT of 99.8% purity was obtained. The yield was 92.1%.

EXAMPLE 5

100 g (0.510 mol) of 2-trifluormethylbenzal fluoride was used as the starting compound, and the process of Example 1 was repeated except that the quantity of the 15 wt % solution of sodium hydroxide was increased to 327 g. As the reasult 77.6 g of 2-TFMT of 99.5% purity was obtained. The yield was 91.7%.

EXAMPLE 6

100 g (0.471 mol) of 2-monochloromonofluoromethyl-benzotrifluoride was used as the starting compound, and the process of Example 1 was repeated except that the quantity of the 15 wt % solution of sodium hydroxide was increased to 301 g. The product was 70.0 g of 2-TFMT of 99.3 % purity. The yield was 92.2%.

EXAMPLE 7

100 g (0.433 mol) of 4-monochlorodifluoromethyl-benzotrifluoride was used as the starting compound, and the process of Example 1 was repeated except the quantity of the 15 wt % solution of sodium hydroxide was increased to 312 g. The product was 64.3 g of 4-TFMT of 99.6% purity. The yield was 92.3%.

EXAMPLE 8

The autoclave used in Example 1 was charged with 100 g (0.467 mol) of 1,4-bis(trifluoromethyl)benzene, 280 g of 20 wt % aqueous solution of sodium hydroxide and 5 g of the palladium-on-carbon catalyst (Pd 5 wt %). Then hydrogenation reaction was carried out for 12 hr generally in the same manner as in Example 1, but in this case the reaction temperature was 115°–121° C. and the hydrogen gas pressure was maintained at 10 kg/cm$^2$. After the reaction, removal of the catalyst and separation of organic matter were done in the same manner as in Example 1. The obtained organic product contained 55.8% of 4-TFMT, 23.1% of 4-xylene and 20.5% of unreacted 1,4-bis(trifluoromethyl)benzene. This crude product was subjected to precision distillation under normal pressure to threby obtain 45.8 g of 4-TFMT of 97.5% purity. The yield was 59.8%.

EXAMPLE 9

The process of Example 8 was modified only in that 78.4 g of potassium hydroxide was used in place of sodium hydroxide, that the quantity of the catalyst was increased to 10 g and that the reaction time was shortened to 7 hr. As the result 47.9 g of 4-TFMT of 97.3% purity was obtained.

EXAMPLE 10

100 g of 1,3-bis(trifluoromethyl)benzene was used as the starting HMBTF. Otherwise the process of EXample 9 was repeated. As the result 46.4 g of 3-TFMT of 97.0% purity was obtained. The yield was 60.2%.

EXAMPLE 11

The autoclave used in Example 1 was charged with 75 g 1,4-bis(trifluoromethyl)benzene, 315 g of 20 wt % aqueous solution of potassium hydroxide and 7.5 g of palladium-on-carbon catalyst (Pd 5 wt %). Then hydrogenation reaction was carried out for 6 hr generally in the same manner as in Example 1, but in this case the reaction temperture was 100° C. and the hydrogen gas pressure was maintained at 13 kg/cm². After the reaction the catalyst was filtered out, and the filtrate was allowed to separate into an aqueous layer and an organic layer.

The organic layer contained 55.0% of 4-TFMT, 18.6% of 4-xylene and 25.2% of unreacted 1,4-bis(trifluoromethyl)benzene. That is, in the hydrogenation reaction the selectivity to TFMT was 74.7%. The obtained organic mixture was subjected to precision distillation, but the purity of the isolated 4-TFMT did not exceed 98%.

EXAMPLE 12

The process of Example 11 was repeated except that 3.8 g of potassium fluoride was added to the materials initially charged in the autoclave.

In this case the crude organic product contained 40.3% of 4-TFMT, 6.0% of 4-xylene and 53.0% of unreacted 1,4-bis(trifluoromethyl)benzene. That is, in the hydrogenation reaction the selectivity to TFMT was 87.0%.

The obtained organic mixture was kept cooled with ice, and 13.8 g of 25% fuming sulfuric acid was added, followed by stirring for 1 hr. After this sulfonation treatment the liquid mixture was allowed to separate into two layers to thereby recover organic matter. There was no trace of 4-xylene in the recovered organic matter, meaning that 100% removal of 4-xylene was accomplished by the sulfonation treatment. After drying with molecular sieves the organic matter was subjected to simple distillation to obtain 23.0 g of 4-TFMT of 99.8% purity. The overall yield of 4-TFMT was 41.0%.

EXAMPLE 13

The process of Example 12 was modified only in that 0.75 g of methanol was used in place of potassium fluoride and that the hydrogen gas pressure was lowered to 3 kg/cm². In this case the crude organic product contained 40.4% of 4-TFMT, 5.0% of 4-xylene and 54.4% of unreacted 1,4-bis(trifluoromethyl)benzene. That is, the selectivity to TFMT was 89.0%. Using 11.5 g of 25% fuming sulfuric acid, sulfonation treatment of the crude product was made in the same manner as in Example 12 to thereby remove 4-xylene. After that the recovered organic matter was subjected to simple distillation to obtain 26.3 g of 4-TFMT of 99.9% purity. The overall yield of 4-TFMT was 46.5%.

EXAMPLE 14

75 g of 1,3-bis(trifluoromethyl)benzene was used as the starting material. Otherwise the hydrogenation process of Example 12 was repeated. In this case the crude organic product contained 55.1% of 3-TFMT, 5.9% of 3-xylene and 39.0% of unreacted 1,3-bis(trifluoromethyl)benzene. So, the selectivity to TFMT was 90.3%. At room temperature 5.0 g of chlorosulfonic acid was added to the crude product, followed by stirring for 30 min. The resultant liquid mixture was separated into two layers to recover organic matter not containing 3-xylene. By simple distillation of the recovered organic matter 35.5 g of 3-TFMT of 99.9% purity was obtained. The overall yield of 3-TFMTT was 63.3%.

What is claimed is:

1. A process of preparing trifluoromethyltoluene, comprising the step of reacting a halomethylbenzo-trifluoride with hydrogen gas in the presence of an acid acceptor and a hydrogenation catalyst to thereby hydrogenate the halomethyl group of the halomethyl-benzotrifluoride to methyl group.

2. A process according to claim 1, wherein said halomethylbenzotrifluoride is a compound represented by the following general formula:

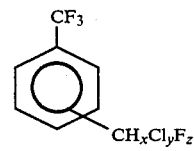

wherein x is 0, 1, or 2, y is 0, 1, 2 or 3 and z is 0, 1, 2 or 3, with proviso that the sum of x, y and z is 3.

3. A process according to claim 1, wherein the hydrogenation reaction is carried out in water.

4. A process according to claim 1, wherein the hydrogenation reaction is carried out in an organic liquid which is inactive to the reactants and the reaction product.

5. A process according to claim 1, wherein said acid acceptor is a metal salt selected from the group consisting of hydroxides, carbonates and acetates of alkali metals and hydroxides, oxides, carbonates and acetates of alkaline earth metals.

6. A process according to claim 1, wherein said hydrogenation catalyst comprises a metal selected from the group consisting of palladium, platinum and nickel.

7. A process according to claim 1, wherein the hydrogenation reaction is carried out at a temperature in the range from 4° to 150° C.

8. A process according to claim 7, wherein the hydrogenation reaction is carried out under a hydrogen gas pressure in the range from 1 to 50 kg/cm².

9. A process according to claim 1, wherein said halomethylbenzotrifluoride is bis(trifluoromethyl)benzene and the hydrogenation reaction is carried out in the presence of an alcohol to thereby suppress formation of xylene as a by-product.

10. A process according to claim 9, wherein said alcohol has not more than six carbon atoms.

11. A process according to claim 9, wherein said alcohol amounts to 0.1-10 wt % of said bis(trifluoromethyl)benzene.

12. A process according to claim 9, further comprising the step of treating a crude organic product of the hydrogenation reaction with a sulfonating agent to sulfonate and remove xylene contained in said product.

13. A process according to claim 12, wherein said sulfonating agent is selected from the group consisting of sulfuric acid, fuming sulfuric acid and chlorosulfonic acid.

14. A process according to claim 1, wherein said halomethylbenzotrifluoride is bis(trifluoromethyl)benzene and the hydrogenation reaction is carried out in the presence of an alkali metal fluoride to thereby suppress formation of xylene as a by-product.

15. A process according to claim 14, wherein said alkali metal fluoride is selected from the group consisting of sodium fluoride and potassium fluoride.

16. A process according to claim 14, wherein said alkali metal fluoride amounts to 3–10 wt % of said bis(trifluoromethyl)benzene.

17. A process according to claim 1, wherein said halomethylbenzotrifluoride is bis(trifluoromethyl)benzene, the process further comprising the step of treating a crude organic product of the hydrogenation reaction with a sulfonating agent to sulfonate and remove xylene contained in said product.

* * * * *